(12) United States Patent
Riley (10) Patent No.: US 11,696,861 B1
(45) Date of Patent: Jul. 11, 2023

(54) CRIB BEDDING WITH TEMPERATURE GAUGE

(71) Applicant: Kendrick L. Riley, Kissimmee, FL (US)

(72) Inventor: Kendrick L. Riley, Kissimmee, FL (US)

( * ) Notice: Subject to any disclaimer, the term of this patent is extended or adjusted under 35 U.S.C. 154(b) by 388 days.

(21) Appl. No.: 16/901,354

(22) Filed: Jun. 15, 2020

(51) Int. Cl.
| | | |
|---|---|---|
| *A61G 7/05* | (2006.01) | |
| *A47C 27/12* | (2006.01) | |
| *A47D 15/00* | (2006.01) | |
| *A47C 21/04* | (2006.01) | |
| *A47G 9/02* | (2006.01) | |

(52) U.S. Cl.
CPC .............. *A61G 7/05* (2013.01); *A47C 21/048* (2013.01); *A47C 27/12* (2013.01); *A47D 15/001* (2013.01); *A47G 9/0215* (2013.01); *A61G 2200/14* (2013.01); *A61G 2203/12* (2013.01); *A61G 2203/20* (2013.01); *A61G 2203/46* (2013.01); *A61G 2203/70* (2013.01)

(58) Field of Classification Search
CPC ............ A61G 2203/12; A61G 2203/20; A61G 2203/46; A61G 2203/70; A61G 2200/14; A61G 7/05; A47C 27/12; A47C 27/16; A47C 21/04; A47C 21/048; A47C 31/105; A47D 15/00; A47D 15/001; A47G 9/0215; A47G 9/0246; H05B 3/36; A61F 7/007; A61F 7/0097
See application file for complete search history.

(56) References Cited

U.S. PATENT DOCUMENTS

| | | | | |
|---|---|---|---|---|
| 2,606,996 | A * | 8/1952 | Westerberg | ............ H05B 3/342 |
| | | | | 219/217 |
| 3,683,151 | A * | 8/1972 | Mills | .................. G05D 23/1909 |
| | | | | 219/501 |
| 4,066,072 | A | 1/1978 | Cummins | |
| 4,656,334 | A * | 4/1987 | Endo | ..................... A47C 21/048 |
| | | | | 219/505 |
| 4,736,088 | A * | 4/1988 | Bart | ........................ A61F 13/00 |
| | | | | 219/211 |
| 5,446,934 | A | 9/1995 | Frazier | |
| 5,451,747 | A * | 9/1995 | Sullivan | .................. A61F 7/007 |
| | | | | 219/505 |
| 6,493,888 | B1 | 12/2002 | Salvatini et al. | |
| 6,582,456 | B1 * | 6/2003 | Hand | ....................... A61G 1/00 |
| | | | | 219/217 |
| 6,713,724 | B1 * | 3/2004 | Carr | ....................... H05B 3/342 |
| | | | | 219/549 |
| 6,884,973 | B2 * | 4/2005 | Castracane | .......... H05B 1/0294 |
| | | | | 219/508 |

(Continued)

FOREIGN PATENT DOCUMENTS

BE             1023015 B1 * 11/2016

*Primary Examiner* — David R Hare
(74) *Attorney, Agent, or Firm* — Cramer Patent & Design, PLLC; Aaron R. Cramer (57) ABSTRACT

Bedding for a crib mattress includes a plurality of temperature sensitive sensors disposed therein and an on-board power source. The sensors are configured to be in wireless communication with a monitoring device. A visual indicator is disposed upon the bedding and in electrical communication with the power source. The visual indicator is activated when a pre-set temperature is sensed by any one of the sensors.

20 Claims, 5 Drawing Sheets

(56) References Cited

U.S. PATENT DOCUMENTS

| | | | |
|---|---|---|---|
| 6,924,467 B2 * | 8/2005 | Ellis | A61F 7/007 219/217 |
| 6,933,469 B2 * | 8/2005 | Ellis | A61F 7/00 219/217 |
| 7,107,639 B2 * | 9/2006 | Taricani | A47D 13/08 5/915 |
| 7,189,944 B2 * | 3/2007 | Child | H05B 3/342 219/545 |
| 7,772,528 B2 * | 8/2010 | Lewin | H05B 3/34 219/217 |
| 7,787,726 B2 * | 8/2010 | Ten Eyck | A47G 9/0223 5/482 |
| 7,827,631 B2 | 11/2010 | Holman | |
| 8,583,206 B2 | 11/2013 | Brauers et al. | |
| 9,095,008 B1 * | 7/2015 | Seacord | H05B 3/34 |
| 9,138,190 B2 | 9/2015 | Liu et al. | |
| 9,320,363 B1 | 4/2016 | Beaver | |
| 10,206,248 B2 | 2/2019 | Augustine et al. | |
| 10,438,475 B2 | 10/2019 | Williams | |
| 10,805,988 B2 * | 10/2020 | Howard | H05B 3/342 |
| 10,993,557 B2 * | 5/2021 | Nardo | A47G 9/10 |
| 2002/0117495 A1 * | 8/2002 | Kochman | F24D 13/024 219/549 |
| 2006/0137099 A1 * | 6/2006 | Feher | A47C 7/748 5/713 |
| 2007/0272673 A1 * | 11/2007 | Keane | H05B 3/56 219/217 |

\* cited by examiner

CRIB BEDDING WITH TEMPERATURE GAUGE

RELATED APPLICATIONS

None.

FIELD OF THE INVENTION

The presently disclosed subject matter is directed to bedding for a crib and more specifically to bedding for a crib having a temperature gauge.

BACKGROUND OF THE INVENTION

As any parent will attest, the safety and well-being of their children is of the utmost importance and is by far their primary concern. Unsurprisingly, there are a wide variety of products aimed at providing a safe home environment for children by preventing the accidents and mishaps that occur all too often.

However, one event that strikes most every child perhaps multiple times over their developmental years is that of a fever. Whether as a result of cold or the flu, a child with a fever is a very concerning issue. So much in fact that many parents resort to near continuous monitoring of the child so that additional medical steps can be taken should the fever suddenly spike. However, this continuous fever measurement becomes difficult at night when the child is sleeping, as the contact or prodding by a thermometer is sure to wake them up and ultimately make them feel worse. Accordingly, there exists a need for a means by which a child's internal body temperature can be continuously monitored while the child is sleeping without the disadvantages as described above. The development of the crib bedding with temperature gauge fulfills this need.

SUMMARY OF THE INVENTION

The principles of the present invention provide for a body temperature sensing mattress pad which comprises an upper padded surface, four side panels, an elastic lower edge which assists to retain the mattress pad to a mattress, an electronics enclosure which is disposed on a distal vertical edge of one of the four side panels, a plurality of fasteners which secure the electronics enclosure to the side panels and a plurality of heat sensors which are arranged in a grid like pattern on the upper padded surface of the mattress pad. The heat sensors are interconnected by a set of grid array cables which run in a horizontal, vertical, and diagonal configuration.

The body temperature sensing mattress pad also comprises an upper textile layer made of a soft and breathable material and a next lower layer which includes a heat sensing layer which contains the heat sensors and the grid array cables. The next lower layer is disposed directly underneath the upper textile layer. The body temperature sensing mattress pad also comprises a padding layer which is disposed directly under the heat sensing layer, a lower textile layer which is disposed directly underneath the padding layer and a first indicator light indicating proper operation of the body temperature sensing mattress pad. Proper operation indicates a satisfactory battery level, a proper connection of the electrical connector, and a remote link activation. The body temperature sensing mattress pad also comprises a second indicator light which indicates a high temperature as detected by the heat sensing layer and a battery access door which allows a user to access and to change one or more internal batteries to power the body temperature sensing mattress pad. All of the layers are quilted together while the first indicator light is smaller than the second indicator light.

The body temperature sensing mattress pad may also comprise a waterproof connected to the electronics enclosure. The waterproof tether may terminate in an electrical connector. The electronics enclosure may be removed from the mattress pad by separating the fasteners and disconnecting the electrical connector which allows the mattress pad to be washed and dried while the electronics enclosure remains behind. The electronics enclosure may produce a radio frequency signal which allows the mattress pad to communicate with an external device. The external device may be selected from the group consisting of a smart phone, a tablet computer, a notebook computer, a desktop computer, or a smart home hub.

The electronics enclosure may be five inches tall and three-quarters of an inch thick and may be made of a durable plastic. The fasteners may be hook and loop fasteners. The grid array cables may be multiconductor and may individually terminate at the waterproof tether and the electrical connector. The soft breathable material may be cotton. The padding layer may be made of material selected from the group consisting of polyester fiberfill, wool, cotton, or down. The high temperature would be 100° F. The second indicator light may be red in color and may flash when activated. The one or more batteries may be one or more button style watch batteries and may supply power to a main processor envisioned to be a single board computer.

The main processor may receive input signals from a multiplexer which collects and aggregates the multiple signals from the individual heat sensors. The signals from the heat sensors may be passed on the grid array cables and the waterproof tether and through the electrical connector to the multiplexer for the main processor to analyze and review the signals from the heat sensor to determine excessive temperature. The main processor may provide one or more output signals to the small indicator light, the large indicator light and a radio frequency transmitter. The radio frequency transmitter may use an antenna located internal to the electronics enclosure to produce the radio frequency signal.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY 10 body temperature sensing mattress pad
15 upper padded surface
20 side panel
25 elastic lower edge
30 electronics enclosure
35 waterproof tether
40 electrical connector
45 fastener
50 heat sensor
55 grid array cable
60 upper textile layer
65 heat sensing layer
70 padding layer
75 lower textile layer
80 small indicator light
85 large indicator light
90 battery access door
95 radio frequency (RF) signal
100 button cell battery
105 main processor
110 multiplexer
115 radio frequency transmitter
120 antenna

DESCRIPTION OF THE PREFERRED EMBODIMENTS

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Figure 1:
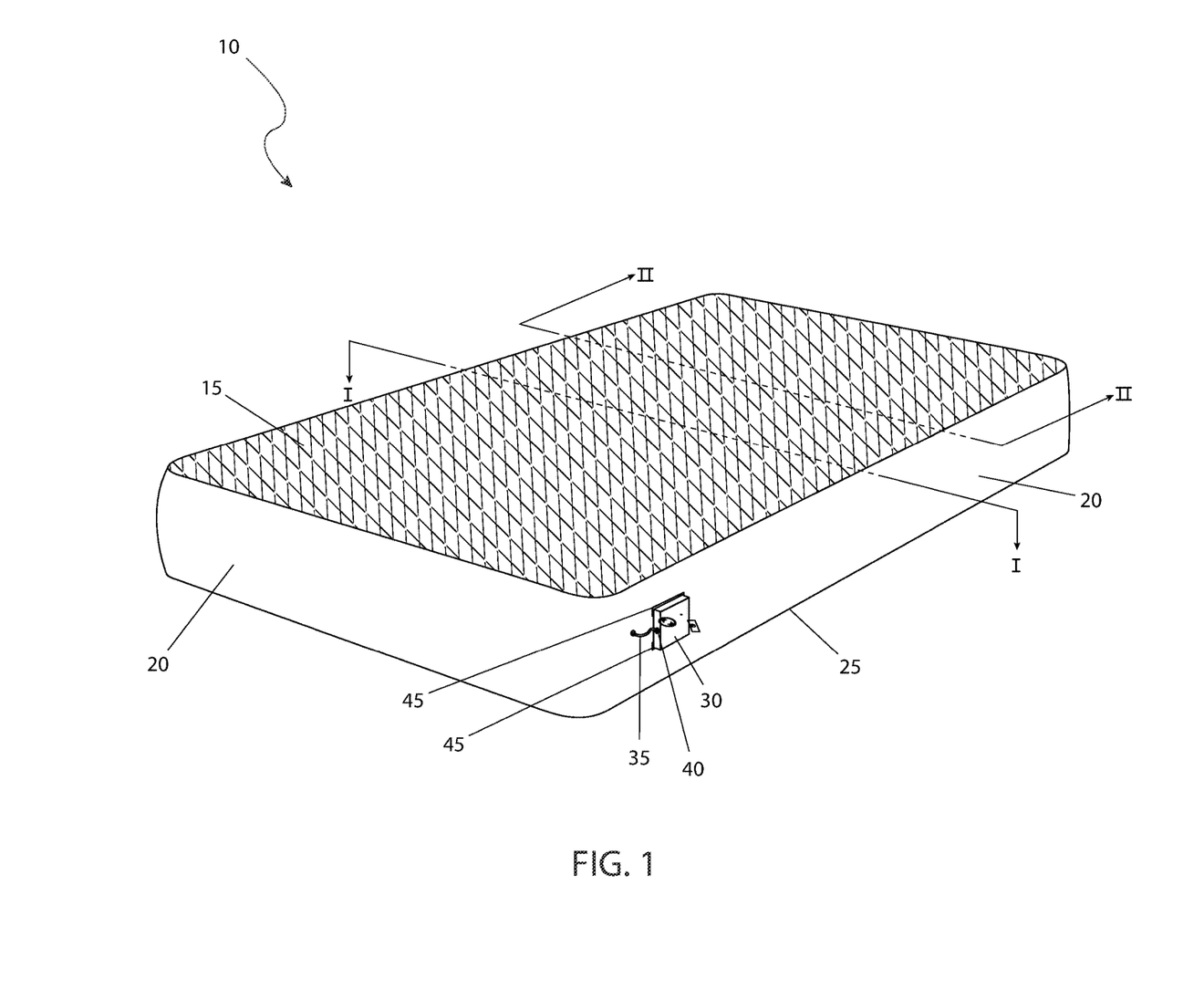
FIG. 1 is a perspective view of the body temperature sensing mattress pad, according to the preferred embodiment of the present invention.

Referring now to FIG. 1, a perspective view of the body temperature sensing mattress pad 10, according to the preferred embodiment of the present invention is disclosed. The body temperature sensing mattress pad 10 (herein also described as the "mattress pad") 10, provides visual and remote alerts for a user's temperature that exceeds a predetermined set-point. While specifically envisioned for use on a crib mattress with a young child, the invention may be used on any style or size of mattress. As such, the specific size or dimensions of the mattress pad 10 are not intended to be a limiting factor of the present invention. The mattress pad 10 provides for an consists of an upper padded surface 15, four (4) side panels 20 (of which only two (2) are shown due to illustrative limitations) and an elastic lower edge 25 to assist in retaining the mattress pad 10 to a mattress during use. An electronics enclosure 30 is provided at a distal vertical edge of one of the side panels 20. Further description of the contained components and functionality of the electronics enclosure 30 will be provided herein below. A waterproof tether 35, terminating in an electrical connector 40, is connected into the electronics enclosure 30. A set of fasteners 45, such as Velcro®, is used to secure the electronics enclosure 30 to the side panels 20. It is envisioned that the electronics enclosure 30 can be removed from the mattress pad 10 by separating the fastener 45 and disconnecting the electrical connector 40, thus allowing the mattress pad 10 to be washed and dried while the electronics enclosure 30 remains behind.

Figure 2:
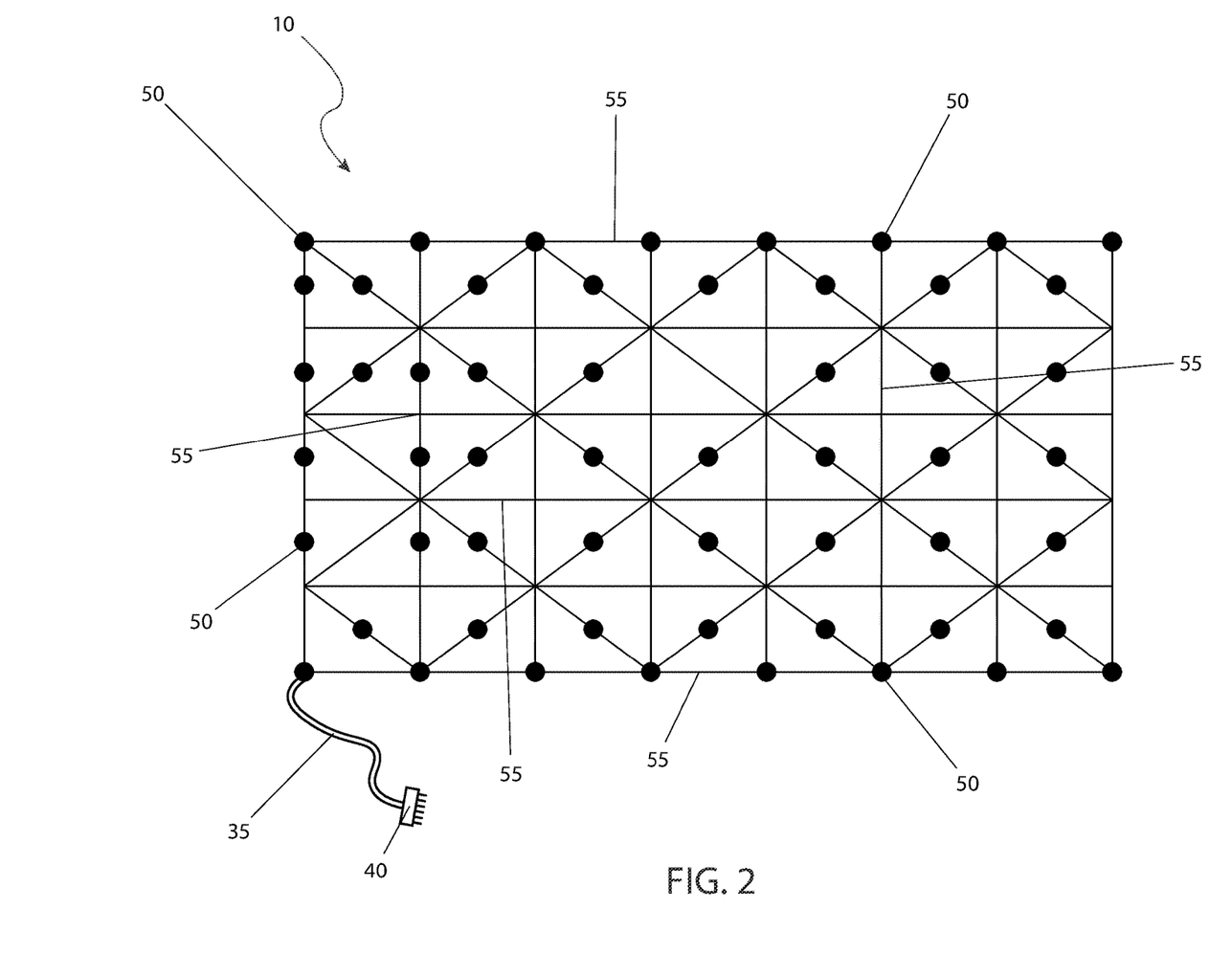
FIG. 2 is a sectional view of the body temperature sensing mattress pad, as seen along a line I-I, as shown in FIG. 1, according to the preferred embodiment of the present invention.

Referring next to FIG. 2, a sectional view of the mattress pad 10, as seen along a line I-I, as shown in FIG. 1, according to the preferred embodiment of the present invention is depicted. This view discloses a plurality of heat sensors 50 arranged in a grid like pattern on the upper surface of the mattress pad 10. It is envisioned that the total quantity of heat sensors 50 will vary depending on the overall size of the mattress upon which the mattress pad 10 is utilized, with a small quantity used for a crib mattress, and a larger quantity used for a king-sized mattress. The heat sensors 50 are interconnected by a set of grid array cables 55, running in a horizontal, vertical, and diagonal configuration as shown. Such grid array cables 55 are envisioned to be multiconductor and will all individually terminate at the waterproof tether 35 and ultimately the electrical connector 40.

Figure 3:
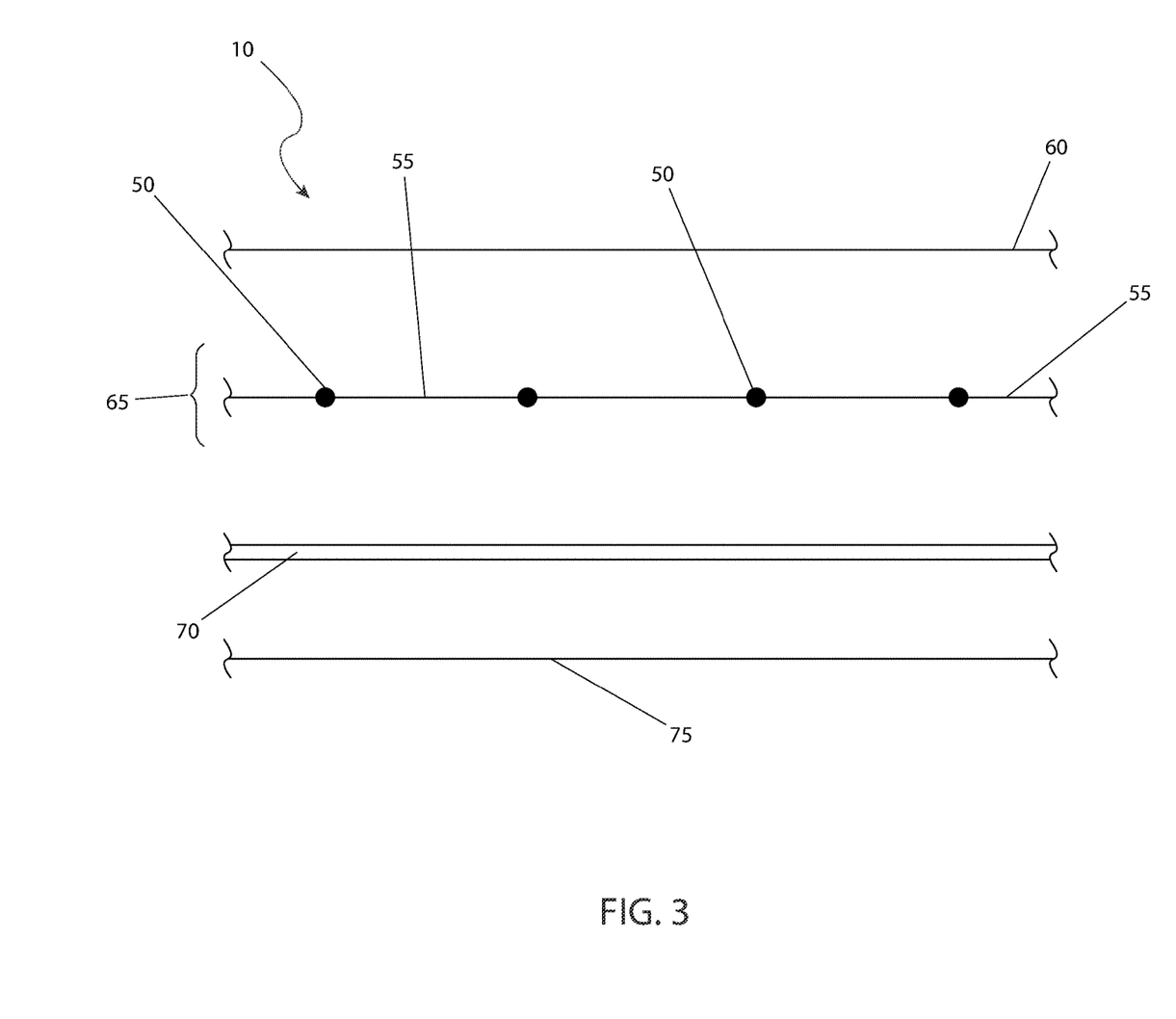
FIG. 3 is a sectional view of the body temperature sensing mattress pad, as seen along a line II-II, as shown in FIG. 1, according to the preferred embodiment of the present invention.

Referring now FIG. 3, a sectional view of the mattress pad 10, as seen along a line II-II, as shown in FIG. 1, according to the preferred embodiment of the present invention is shown. The uppermost layer of the mattress pad 10 comprises an upper textile layer 60, envisioned to be of a soft breathable material such as cotton. The next lower layer comprises the heat sensing layer 65 containing the heat sensors 50 and the grid array cables 55. Directly under the heat sensing layer 65 is a padding layer 70, envisioned to be made of polyester fiberfill, wool, cotton, or down. On the bottom, a lower textile layer 75 is provided. It is envisioned that the upper textile layer 60 would be made of the same materials as the upper textile layer 60, but perhaps of a lower quality, such as a lower thread count. It is envisioned that all layers will be quilted together during final assembly.

Figure 4:
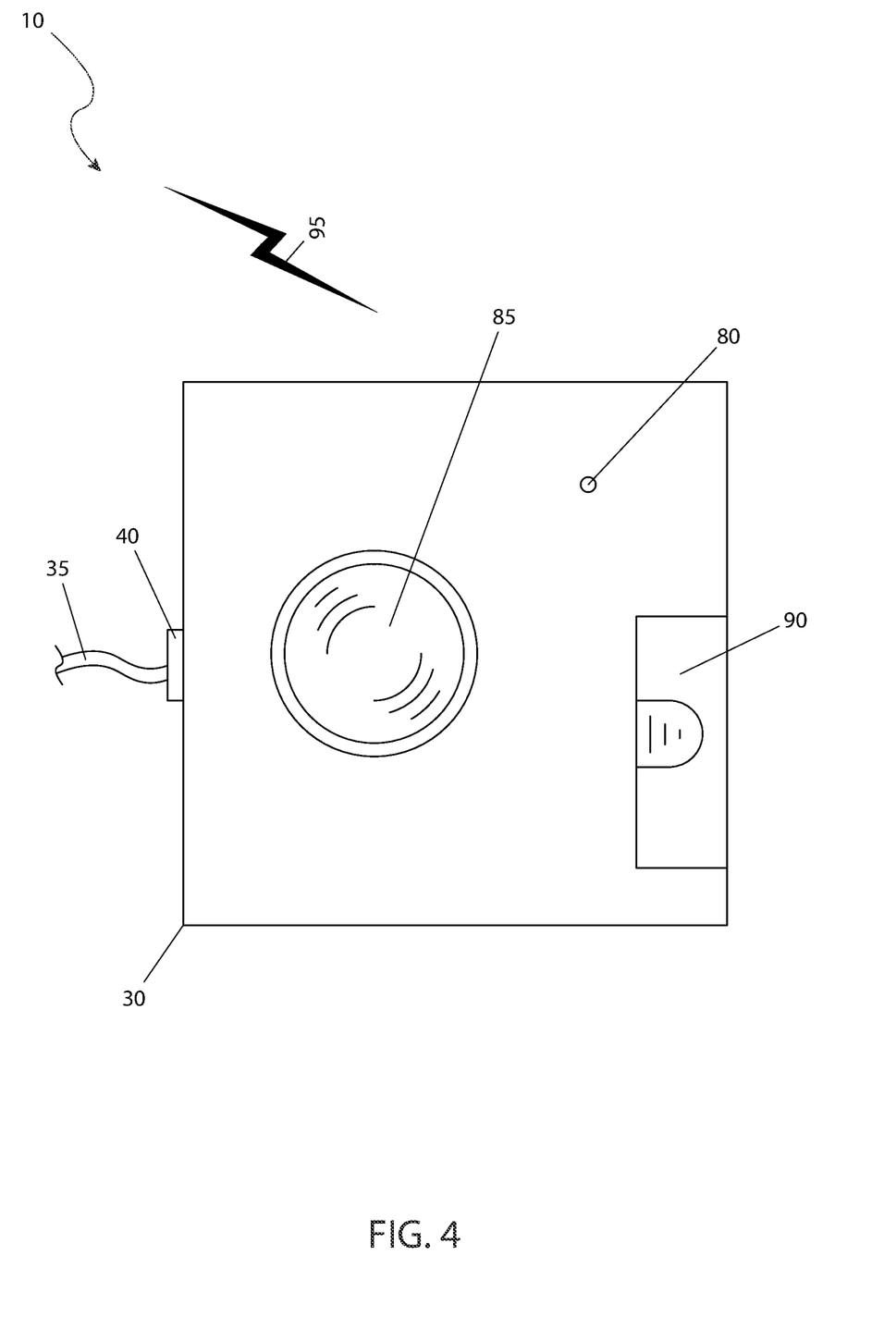
FIG. 4 is a detailed view of the electronics enclosure as used with the body temperature sensing mattress pad, according to the preferred embodiment of the present invention; and, FIG. 5 is an electrical block diagram of the body temperature sensing mattress pad, according to the preferred embodiment of the present invention.

Referring next to FIG. 4, a detailed view of the electronics enclosure 30 as used with the body temperature sensing mattress pad 10, according to the preferred embodiment of the present invention is disclosed. The electronics enclosure 30 is envisioned to be approximately five inches (5 in.) tall, five inches (5 in.) tall and three-quarters of an inch (¾ in.) thick and made of a durable plastic. The waterproof tether 35 and the electrical connector 40 is shown entering on the left via the electrical connector 40. A small indicator light 80 indicates proper operation such satisfactory battery level, proper connection of the electrical connector 40, remote link activation and the like. A large indicator light 85 provides indication of a high temperature as detected by the heat sensing layer 65 (as shown in FIG. 2 and FIG. 3). It is envisioned that the high temperature would be one hundred degrees Fahrenheit (100° F.; 37.7° C.). The large indicator light 85 is envisioned to be red in color and will flash when activated to aid in its attention gathering characteristics. A battery access door 90 provides the ability to access and change internal batteries, envisioned to the be of the button style watch batteries, which operate the mattress pad 10. The electronics enclosure 30 produces a radio frequency (RF) signal 95 which allows the mattress pad 10 to communicate with external devices including but not limited to smart phones, tablet computers, notebook computers, desktop computers, smart home hubs, and the like. Further description of the radio frequency (RF) signal 95 and associated components will be provided herein below.

Figure 5:
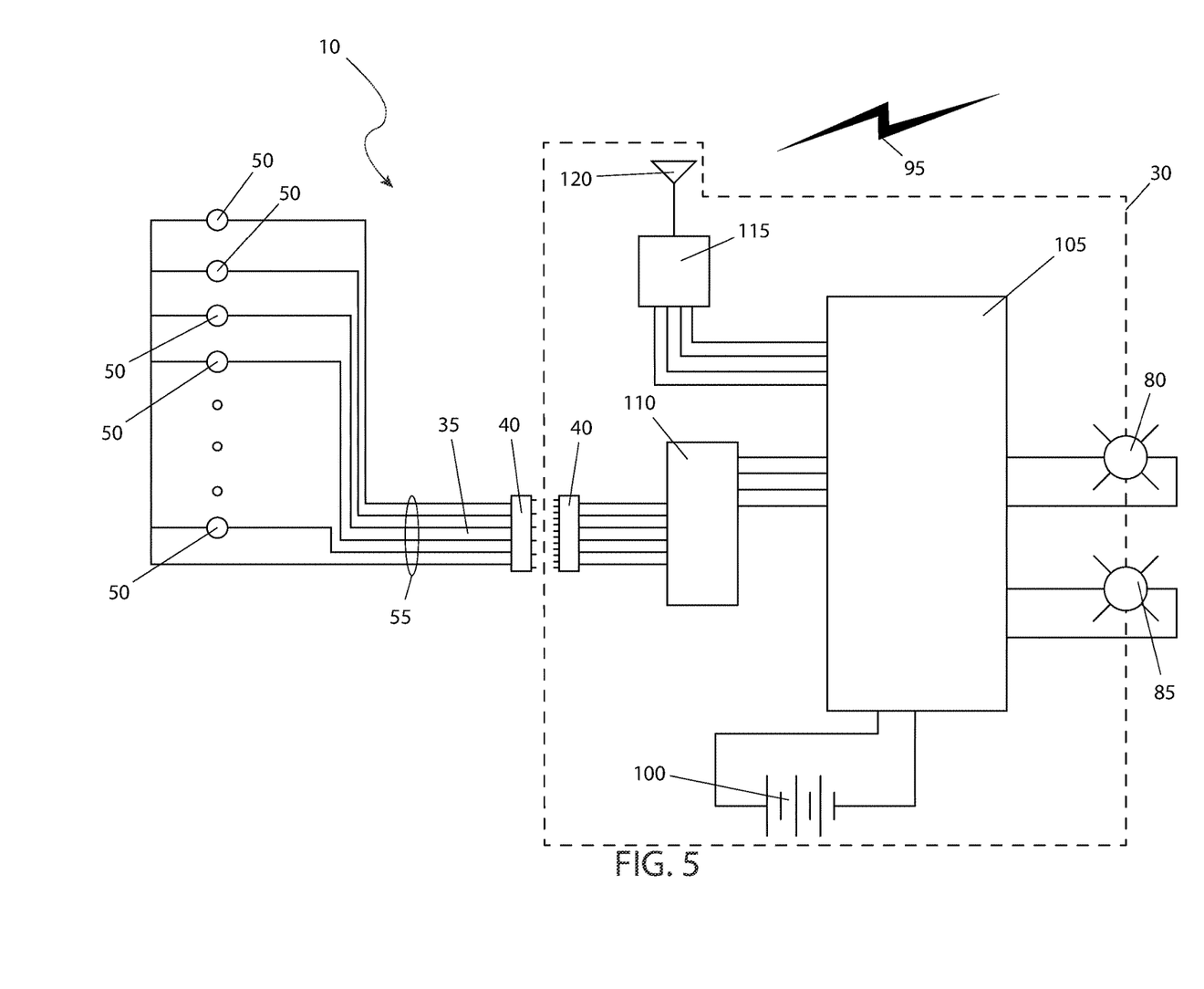

Referring to FIG. 5, an electrical block diagram of the body temperature sensing mattress pad 10, according to the preferred embodiment of the present invention is depicted. Electrical power for the mattress pad 10 is provided by multiple button cell batteries 100 which supplies power to a main processor 105 envisioned to be a single board computer (SBC) such as an Arduino or Raspberry Pi®. The main processor 105 receives input signals from a multiplexer 110 which collects and aggregates the multiple signals from the individual heat sensors 50. The signal from the heat sensors 50 are passed on the grid array cables 55 and the waterproof tether 35 and through the electrical connector 40 to the multiplexer 110. The main processor 105 then analyzes and reviews the signals from the heat sensors 50 to determine excessive temperature as defined above. The main processor 105 then provides output signals to the small indicator light 80, the large indicator light 85 and a radio frequency transmitter 115 as appropriate. The radio frequency transmitter 115 then uses an antenna 120, located internal to the electronics enclosure 30 to produce the radio frequency (RF) signal 95.

2. Operation of the Preferred Embodiment

The preferred embodiment of the present invention can be utilized by the common user in a simple and effortless manner with little or no training. It is envisioned that the mattress pad 10 would be constructed in general accordance with FIG. 1 through FIG. 5. The user would procure the mattress pad 10 from conventional procurement channels such as department stores, discount stores, bedding and linen stores, children's goods stores, mail order and interne supply houses and the like. Special attention would be paid to the overall size of the mattress upon which the mattress pad 10 is to be used.

After procurement and prior to utilization, the mattress pad 10 would be prepared in the following manner: the mattress pad 10 would be applied to the mattress following the same application methods as conventional bed linens, the electronics enclosure 30 would be attached to the side panels 20 using the fastener 45, the waterproof tether 35 and electrical connector 40 would be connected into the electronics enclosure 30; button cell batteries 100 would be installed in the electronics enclosure 30 by removal of the battery access door 90; and proper operation of the mattress pad 10 would be verified by illumination of the small indicator light 80.

During utilization of the mattress pad 10, the following procedure would be initiated: the user of the mattress pad 10, be it a small child on a crib mattress, or a full-grown adult on a regular mattress, would sleep upon the mattress pad 10 in a transparent manner when compared to a conventional mattress pad. Should the user experience a fever, the heat sensors 50 will detect the high temperature and transmit said signal to the electronics enclosure 30 whereupon the main processor 105 will issue a visual alert to the large indicator light 85 as well as an radio frequency (RF) signal 95 to any connected smart phones, tablet computers, notebook computers, desktop computers, smart home hubs, and the like. The alert signal will notify parents or care providers to take corrective action.

After use of the mattress pad 10, it may be washed by disconnecting the electrical connector 40 and the waterproof tether 35 from the electronics enclosure 30; removing the electronics enclosure 30 from the side panels 20 via the separation of the fastener 45; and washing and drying the mattress pad 10 in a conventional manner. It may then be reapplied to the mattress following the above-mentioned process and used again in a repeating cyclical manner.

The features of the body temperature sensing mattress pad 10 allow a parent or care provider to continuously monitor the user's body temperature while he or she sleeps without worry of waking them up to take their temperature. As such, said usage allows a sleeping individual to be continuously monitored for a high temperature in a manner which does intrude upon or aggravate the user while ensuring physical health and medical well-being.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A body temperature sensing mattress pad, comprising:
an upper padded surface;
four side panels;
an elastic lower edge assisting to retain the mattress pad to a mattress;
an electronics enclosure disposed on a distal vertical edge of one of the four side panels;
a plurality of fasteners securing the electronics enclosure to the side panels;
a plurality of heat sensors arranged in a grid like pattern on the upper padded surface of the mattress pad, the heat sensors are interconnected by a set of grid array cables running in a horizontal, vertical, and diagonal configuration;
an upper textile layer made of a soft breathable material;
a next lower layer including a heat sensing layer containing the heat sensors and the grid array cables, the next lower layer disposed directly underneath the upper textile layer;
a padding layer disposed directly under the heat sensing layer;
a lower textile layer disposed directly underneath the padding layer;
a first indicator light disposed upon the electronics enclosure indicating proper operation of the body temperature sensing mattress pad including a battery charge level, a proper connection of the electrical connector, and a remote link activation;
a second indicator light disposed upon the electronics enclosure indicating a high temperature as detected by the heat sensing layer; and
a battery access door light disposed upon the electronics enclosure allowing a user to access and to change one or more internal batteries to power the body temperature sensing mattress pad;
wherein all of the layers are quilted together; and
wherein the first indicator light is smaller than the second indicator light.

2. The body temperature sensing mattress pad, according to claim 1, further comprising a waterproof tether connected to the electronics enclosure.

3. The body temperature sensing mattress pad, according to claim 2, wherein the waterproof tether terminates in an electrical connector.

4. The body temperature sensing mattress pad, according to claim 3, wherein the electronics enclosure is removed from the mattress pad by separating the fasteners and disconnecting the electrical connector allowing the mattress pad to be washed and dried while the electronics enclosure remains behind.

5. The body temperature sensing mattress pad, according to claim 1, wherein the electronics enclosure produces a radio frequency signal which allows the mattress pad to communicate with an external device.

6. The body temperature sensing mattress pad, according to claim 5, wherein the external device is selected from the group consisting of a smart phone, a tablet computer, a notebook computer, a desktop computer, and a smart home hub.

7. The body temperature sensing mattress pad, according to claim 1, wherein the electronics enclosure is five inches tall and three-quarters of an inch thick.

8. The body temperature sensing mattress pad, according to claim 1, wherein the electronics enclosure is made of a durable plastic.

9. The body temperature sensing mattress pad, according to claim 1, wherein the fasteners are hook and loop fasteners.

10. The body temperature sensing mattress pad, according to claim 3, wherein the grid array cables are multiconductor and individually terminate at the waterproof tether and the electrical connector.

11. The body temperature sensing mattress pad, according to claim 1, wherein the soft breathable material is cotton.

12. The body temperature sensing mattress pad, according to claim 1, wherein the padding layer is made of material selected from the group consisting of polyester fiberfill, wool, cotton, and down.

13. The body temperature sensing mattress pad, according to claim 1, wherein the high temperature is 100° F.

14. The body temperature sensing mattress pad, according to claim 1, wherein the second indicator light is red in color and flashes when activated.

15. The body temperature sensing mattress pad, according to claim 1, wherein the one or more batteries are one or more button style watch batteries.

16. The body temperature sensing mattress pad, according to claim 15, wherein the one or more button style watch batteries supplies power to a main processor.

17. The body temperature sensing mattress pad, according to claim 16, wherein the main processor receives input signals from a multiplexer which collects and aggregates the input signals from the plurality of heat sensors.

18. The body temperature sensing mattress pad, according to claim 17, wherein the signals from the heat sensors are passed on the grid array cables and the waterproof tether and through the electrical connector to the multiplexer for the main processor to analyze and review the signals from the plurality of heat sensors to determine high temperature.

19. The body temperature sensing mattress pad, according to claim 18, wherein the main processor provides one or more output signals to the first indicator light, the second indicator light and a radio frequency transmitter.

20. The body temperature sensing mattress pad, according to claim 19, wherein the radio frequency transmitter uses an antenna located internal to the electronics enclosure to produce the radio frequency signal.

\* \* \* \* \*